United States Patent [19]
Fontenot

[11] Patent Number: 5,980,249
[45] Date of Patent: Nov. 9, 1999

[54] METHOD AND DEVICE FOR TREATMENT OF DENTITION

[75] Inventor: Mark G. Fontenot, Lafayette, La.

[73] Assignee: FOLH, LLC

[21] Appl. No.: 09/096,209

[22] Filed: Jun. 11, 1998

Related U.S. Application Data

[63] Continuation-in-part of application No. 08/694,445, Aug. 12, 1996, Pat. No. 5,863,202, which is a continuation-in-part of application No. 08/213,039, Mar. 15, 1994, Pat. No. 5,575,654, which is a continuation-in-part of application No. 07/980,635, Nov. 24, 1992, abandoned.

[51] Int. Cl.$^6$ .................................................... A61G 17/02
[52] U.S. Cl. ............................................. 433/80; 433/215
[58] Field of Search ..................... 433/215, 216, 433/80, 6; 128/860, 861, 862; 206/63.5, 83

[56] References Cited

U.S. PATENT DOCUMENTS

| | | | |
|---|---|---|---|
| 4,173,505 | 11/1979 | Jacobs | 433/89 |
| 5,063,940 | 11/1991 | Adell et al. | 128/861 |
| 5,165,424 | 11/1992 | Silverman | 128/861 |
| 5,575,654 | 11/1996 | Fontenot | 433/215 |

Primary Examiner—Nicholas D. Lucchesi
Attorney, Agent, or Firm—Lynette Wylie

[57] ABSTRACT

A dental appliance being adaptable to fit a range of variously sized dental arches composed of a polymeric material that preferably comprises a hydrophilic foam, in which a medicinal agent such as, for example, carbamide peroxide, in dry or hydrated form, may be incorporated or predispensed. In one embodiment of the invention, the appliance may be provided in packaging, or medicinal agent may be provided in a separate dispenser that minimizes or prevents permeation by water.

22 Claims, 3 Drawing Sheets

METHOD AND DEVICE FOR TREATMENT OF DENTITION

This is a continuation in part of application Ser. No. 08/694,445 filed on Aug. 12, 1996, now U.S. Pat. No. 5,863,202 which is a continuation in part of application Ser. No. 08/213,039 filed on Mar. 15, 1994 and issued as U.S. Pat. No. 5,575,654 on Nov. 19, 1996, which is a continuation in part of application Ser. No. 07/980,635 filed on Nov. 24, 1992, now abandoned.

FIELD OF THE INVENTION

This invention relates to dental treatments, particularly involving the delivery of premeasured amounts of dental bleaching agents and other medicaments with a disposable dental appliance adaptable to fit a a range of variously sized dental arches provided in a convenient and facile system.

BACKGROUND OF THE INVENTION

Recently, home bleaching has been introduced into the dental health care market for the management of stained or discolored teeth. Such treatments are administered by application of bleaching products that are professionally prescribed and supervised, or purchased over the counter and self-administered.

In both the professional and over the counter markets, home bleaching is a technique utilizing oxidizing agents, such as carbamide peroxide or other peroxy compounds, which are delivered to the dental arch by the patient using a rigid dental appliance which is custom fabricated by a dentist or dental laboratory. Protocols supervised by dental professionals employing home bleaching generally have the patient apply a rigid custom dental appliance for periods of up to 120 minutes per day. The daily applications are administered over several weeks, thereby totaling between 20 to 40 hours of home bleaching time. Over the counter procedures typically call for reduced daily bleaching times of up to one hour, and vary in total treatment times.

The exact origin of home bleaching is unclear. The earliest reports of dental bleaching occurred in the mid-1960's when Glyoxide™, an over-the-counter preparation containing 10 percent carbamide peroxide in glycerin which was used for soft tissue wound healing (commercially available from Marion Merrel Dow, Inc.) was observed to have and used for the desirable side effect of whitening teeth. In 1972, Proxigel™ (commercially available from Reed & Carnrick Pharmacym), was introduced as the agent of choice for whitening teeth. Proxigel™ is a combination of water, glycerin, Carbopol™ (thickening agent) and 10% carbamide peroxide.

The first report of a home bleaching procedure was published in 1989, when Haywood and Heymann reported successful bleaching using Proxigel™ in a custom fabricated dental appliance to be worn at night. In the Haywood and Heymann procedure, the bleaching agent was placed in a soft plastic, vacuum-formed dental appliance for an average of 7.5 hours per night for 2 to 5 weeks. Also in 1989, a White and Brite™ bleaching agent (commercially available through Omni International) became the first system sold specifically for whitening teeth. White and Brite™ is a preparation contain ten per cent carbamide peroxide in glycerine, and is sold exclusively to dentists in conjunction with custom-fitted or prescription dental appliances. Since its introduction into the professional dental health care market, over 20 companies have marketed similar products.

Fabrication of rigid, custom dental appliances entails fabricating stone models of the patient's dental arch impressions, and heating and vacuum-forming a thermoplastic sheet corresponding to the stone models of a patient's dental arches. Thermoplastic films are sold in rigid or semi-rigid sheets, and are available in various sizes and thicknesses. Some manufacturers also may provide laminations of porous foams or low modulus plastics to the rigid thermoplastic films.

In the professional teeth bleaching market, dentists have traditionally utilized one of three types of dental appliances for delivery of home bleaching agents. All three are rigid and custom-fitted to an individual patient's dental arches. The first type is molded to closely fit a patient's dental arches, having no space or lining within the trough for inserting a dental arch.

The second type of rigid custom dental appliance is an "oversized" rigid custom dental appliance, wherein the facial surfaces of the teeth on the stone models are augmented with linings such as die spacers or light cured acrylics. In "oversized" appliances, thermoplastic sheeting is heated and subsequently vacuum formed around the augmented stone models of the dental arch.

The third type of rigid custom dental appliance, which is used with less frequency than the types of appliances described above, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft, porous foam.

Professionally supervised bleaching systems utilizing each of these three varieties of custom-fitted appliances require at least two dental office visits and the fabrication of the rigid custom dental appliance. During the first office visit, the dentist explains the procedure, expected outcome and risks of side effects, and estimated costs of the professionally supervised dental bleaching. If the patient then wishes to proceed, dental impressions are taken and a second office visit is scheduled. During the interim period between the first and second office visits, a rigid custom-fitted dental appliance is fabricated from a thermoplastic sheet vacuum molded to a stone model of the patient's dental impressions. Subsequent to molding the appliance, the excess sheeting is removed and the resulting rigid, custom dental appliance polished and provided to the dentist for fitting to the patient's dental arches. If the patient elects to treat both upper and lower arches, a separate dental appliance for each arch must be fabricated.

At the second office visit, the dentist delivers the first bleaching treatment and instructs the patients on the proper procedure to dispense bleaching agent in the custom appliance. The dentist then provides to the patient a sufficient amount of carbamide peroxide gel to complete the home bleaching regimen prescribed. Typically, the dentist provides several syringes containing about 2 ml to 3 ml of 10 percent to 15 percent carbamide peroxide gel. The patient subsequently applies the bleaching agent daily or as the dentist otherwise prescribes. In the home dental care regimen, the patient dispenses the bleaching agent into the rigid custom dental appliance and then places the appliance over the dental arch for a specified period of time. Typically, the recommended treatment period ranges from 30 to 120 minutes per day. At the end of the treatment period, the dental appliance is removed, thoroughly cleaned to remove any remaining bleaching agent, and then stored until the next application.

Unfortunately, there exist many problems with existing dental bleaching agent treatment systems. As to systems utilizing rigid custom-fabricated dental appliances, the time and expense of forming dental impressions, making the dental appliances and associated dental laboratory work, and multiple office visits are costly and time consuming. Moreover, if a dental appliance is improperly fitted or otherwise defective, a patient may be further inconvenienced by the requirement of additional office visits may be required.

Problems with existing dental treatment regimens are manifold. Conventional rigid, custom-fabricated dental appliances require time-consuming and expensive dentist office visits, dental laboratory tests and fitting of each patient's dentition. Furthermore, any changes in the surface of the patient's teeth, such as filings, crowns, and other accidental or therapeutic alterations of the dentition, would affect the fit of the rigid custom dental appliance and warrant repeating the entire fabrication procedure. Refabrication of the splint may also be required in the event of subsequent rebleaching.

There also exist particular drawbacks with custom bilaminated dental devices, including occlusion and retention of bleaching agent. Furthermore, cleaning and maintenance of foam-lined dental appliances may be problematic, due to the high surface area and pore volume of the foam materials.

Oversized rigid custom dental appliance also have particular drawbacks, including, but not limited to, occlusions in the augmented region, increased appliance fabrication time and cost irritation and the lip of the appliance contacting the gingival region, and decreased retention to the bleaching agent within the target area.

Such and other problems triggered the development of an alternative type of treatment regimen employing self-administered dental bleaching replacing rigid custom dental appliances with disposable soft universal fit, U-shaped appliances. Soft open cell foam trays saturated with a premeasured quantity of bleaching agent (distributed through Cadco Dental Products in Oxnard, Calif. under the tradename VitalWhite™). Recommended treatment protocol described in the product's package insert instructs the patient to fit the device around his or her teeth and to keep the tray in position for sixty minutes after which time it is removed and discarded. Cadco recommends delivery of fourteen sixty-minute applications in a two week period.

Unfortunately, however, side effects of foam appliances used in home bleaching systems have also presented their unique drawbacks. Such foam appliances fail to direct and confine the application of home bleaching agents on the surfaces of a patient's teeth, which is critical to the safety and efficacy of any dental appliance, or other medical device used in or on the human body. Furthermore, the surfaces of such foam devices, which are saturated with bleaching agent are open and exposed to the oral cavity, and allow the elution of large quantities of bleaching agent from the device, enter the oral cavity, and be ingested by the patient. In addition, because of the discomfort associated with the moisture buildup resulting from foaming of the bleaching agent and salivation, patient compliance and acceptance is low.

Such disadvantages include, but are not limited to, the bulk of foam trays of such systems, lack of adequate structural rigidity to fit securely over the dental arches, excessive salivation, and consequent adverse side effects, including hypersensitive reactions and nausea. The likelihood of such side effects is commensurably increases with the strength of the bleaching agent concentration, and is more likely if a patient is unaccustomed to teeth bleaching.

To date, no medicinal agents have been derived to alleviate or attenuate such and other contraindications. Nor have compositions been derived to general, improve the condition of the teeth and mouth, regardless of whether the dentition have been subject to whitening or another dental procedure. Thus, there exist many problems with devices for delivery of home bleaching agents which are presently available.

Additional drawbacks with known systems for treatment of dental arches relate to improper dispensation of agents into dental appliances, particularly when the agents are dispensed by patients who are inexperienced and unaware of the importance of precision and infection control. Improper dispensing may result in overfilling, spillage or incorrect measurement of the agent. Lack of aseptic technique increases the risk of contaminating the bleaching or other medicinal agent into an appliance. Patients who self-administer bleaching or other medicinal agents often fail to provide the careful maintenance, cleaning, and storage which is necessary for a rigid custom dental appliance to perform adequately throughout its entire service life.

Further disadvantages of known bleaching systems relate to dispensing of excessive bleaching or other medicinal agent into the dental appliance which is subsequently displaced from the appliance into the oral cavity, spilled into the mouth, and ingested. Ingestion of significant amounts of bleaching agent may cause the user great discomfort and hypersensitive reactions. The excessive bleaching agent may also cause gingival irritation, burning, edema, nausea and other allergic reactions. A patient may thus ingest The risk of such side effects excessive quantities of bleaching agent increases with the number of treatments, and becomes most significant after the multiple treatments typically required to attain acceptable clinical results. The sponge-like permeability of disposable foam trays merely exacerbates-problems of systems utilizing custom dental appliances resulting from their poor retention or confinement of the bleaching agent to the target area.

Some of the above problems were addressed by the single-step, single use dental appliance and method described in U.S. Pat. No. 5,575,654, a predecessor to the present application. The latter system addresses problems resulting from leakage and hygiene discussed above by utilizing a prefabricated U-shaped dental appliance composed of a nonporous polymer that has a front and rear wall integrally joined at their lower edges to form a trough. As claimed, a predetermined amount of bleaching agent is predispensed in its trough. A layer of open cell foam is preferably affixed to the front and rear walls of the latter appliance.

Although the latter system addressed significant drawbacks relating to leakage and spillage, limitations of this predispensed, prepackaged, single-step dental treatment procedure persist. A particular limitation involves the reduced shelf life and associated efficacy of existing bleaching agents, particularly when predispensed in an appliance. Over a limited period of time, the efficacy of the agent may be attenuated primarily due to moisture in the agent or the surrounding air.

Currently available bleaching agents utilized in both the professional and over the counter markets are either viscous liquids or gels. The peroxy compounds are hydrous and typically provided in gel matrices of differing concentrations. Carbamide peroxide gels dispensed in the professional market range between about 10 to 25 percent while the concentration of carbamide peroxide in over the counter products range between about 6 and 15 percent. Bleaching agents are commercially available and packaged in separate dispensing containers such as bottles and tubes, and most often, gels. The peroxy compounds utilized in the professional and over the counter markets are hydrated and generally provided in gel matrices differing in concentration. Carbamide peroxide gels dispensed in the professional market range between about 10 and 25 percent, while the concentration of carbamide peroxide in over the counter products range between about 6 and 15 percent. When applied at home, the patient dispenses an estimated quantity of bleaching agent to the rigid custom dental appliance, and then places the appliance over the dental arches being treated.

Existing carbamide peroxide systems utilize gels comprising hydrogen peroxide coupled to urea in either anhydrous glycerin base or a soluble, aqueous Carbopol base. When carbamide peroxide is hydrated, the hydrogen peroxide breaks down into urea and peroxide, which subsequently breaks down into water and oxygen. This instability of the agent in hydrated form limits the efficacy of existing bleaching agents, particularly when exposed to water.

This background is not an exhaustive discussion of problems with prior art bleaching systems, but merely exemplifies some prevalent drawbacks encountered with present devices. Therefore, it is apparent that there is a need for substantial improvement in dental treatments involving application of bleach or other medicinal agents to a patient's dentition and periodontal tissue.

SUMMARY OF THE INVENTION

The above and other drawbacks of the prior art are addressed by the present device and method for delivery of bleaching or other medicinal agents to dental arches and surrounding periodontal tissue. This invention provides a U-shaped dental appliance having a trough for immersing the teeth of a user's dental arch composed of a polymeric material that is adaptable to fit a range of variously sized dental arches, which is preferably comprised of a hydrophilic open foam material. Such foam materials may include hydrogel polymers that are chemically imbibed with various agents which, among other things, impart high absorption of fluids.

An alternative embodiment of the present invention features a dental appliance wherein a strip of the hydrophilic open cell foam is affixed along at least a portion of the frontal inner wall of the dental appliance for contacting the anterior portion of the dental arch subject to treatment. A strip of open cell foam may also be affixed along the inner surface of the rear wall of the dental appliance.

In one embodiment of the invention, a dry medicinal agent may be incorporated in the hydrogel foam. The foam thus provides a matrix for application of the medicinal agent when practicing this invention. A medicinal agent administered according to the present invention preferably comprises a dry carbamide peroxide.

As used herein, a medicinal agent is any composition containing a pharmaceutical, bleaching or other dental agent, a nutrition supplement, or other biocompatible compound capable of improving the condition or minimizing untoward side effects of bleaching or other treatments on the dental arches and periodontal tissue. Such compounds may include, but are not limited to, dental bleaching agents, such as carbamide peroxide, antioxidants, such as vitamin E, healing agents such as aloe vera, surfactants for coating the surface of the teeth with a whitener, such as poloaxmer, anti-caries agents such as fluoride, or even dental scrubs which can be brushed to polish the teeth after the treatment of the present invention has been applied. These medicinal agents may be provided in dry or hydrated form.

In practice, the appliance of this invention a user's dental arch is immersed in the trough of the dental appliance containing the medicinal agent. When dry carbamide peroxide is administered with this appliance, the carbamide peroxide powder cascades to hydrogen peroxide and urea due to a reaction of the water in the user's saliva, and bleaching is thereby activated. The hydrophilic foam enhances the user's tolerance and the length of the treatment time by absorbing excess saliva and peroxide.

The present device may be provided in a sealed container that minimizes permeation by or is impermeable to water. In one embodiment, a dry medicinal agent may be incorporated in a foam, as described above, or it may be predispensed in dry or hydrated form. Alternatively, the medicinal agent may be packaged in a separate dispenser such as, for example, a syringe that minimizes permeation by or is impermeable to water. Materials composing such containers may include, but are not limited to, polyvinyl chloride, fluoronated hydrocarbon polymers, and other suitable polymers.

In addition to the significant advantages provided by the prefabricated dental appliance of the predecessor patent of this application, advantages over existing oral dental treatment systems, include the elimination of excess gel that spills out of appliances when displaced by a user's teeth, reduction of excess salivation triggered by the agent due to its absorption by the hydrogel and elimination of the step of predispensing agent when manufacturing the appliance.

DETAILED DESCRIPTION OF THE PREFERRED EMBODIMENTS

Figure 1:
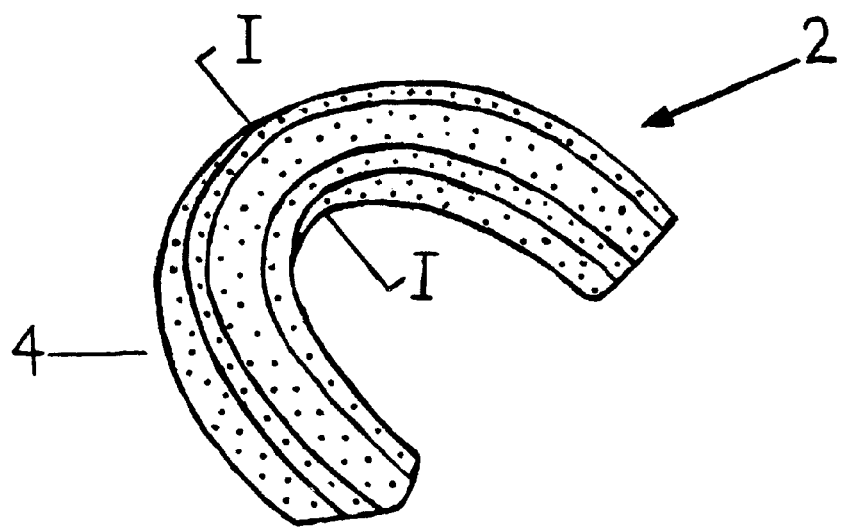
FIG. 1 depicts a perspective view of the dental appliance in accordance with the present invention.
Figure 1A:
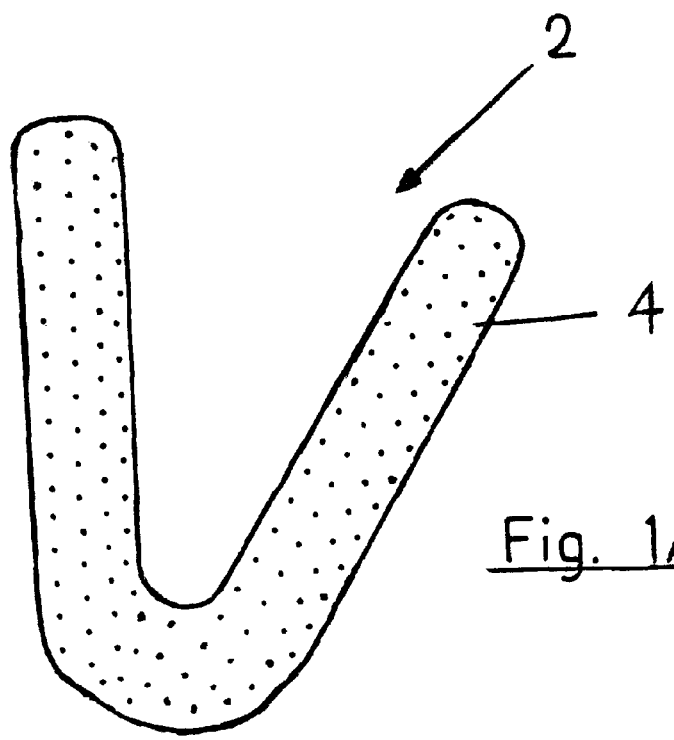
FIG. 1A provides a cross-sectional view of the device of the present invention, taken along line I—I shown in relation to teeth positioned for immersion therein.

Referring to the drawings, the device shown in FIGS. 1 and 1A is a pre-fabricated U-shaped dental appliance 2 having a trough for immersing the teeth which are subject to treatment. In the illustrated embodiment, the dental appliance 2 is fabricated from a hydrophilic open cell foam such as described herein and medicinal agent 4 is a dry carbamide peroxide that is incorporated in the foam, thereby forming a matrix for administering the agent to a user's dentition. In alternative embodiments, dental appliance 2 may be comprised of other suitable open cell foams or polymers.

Figure 2:
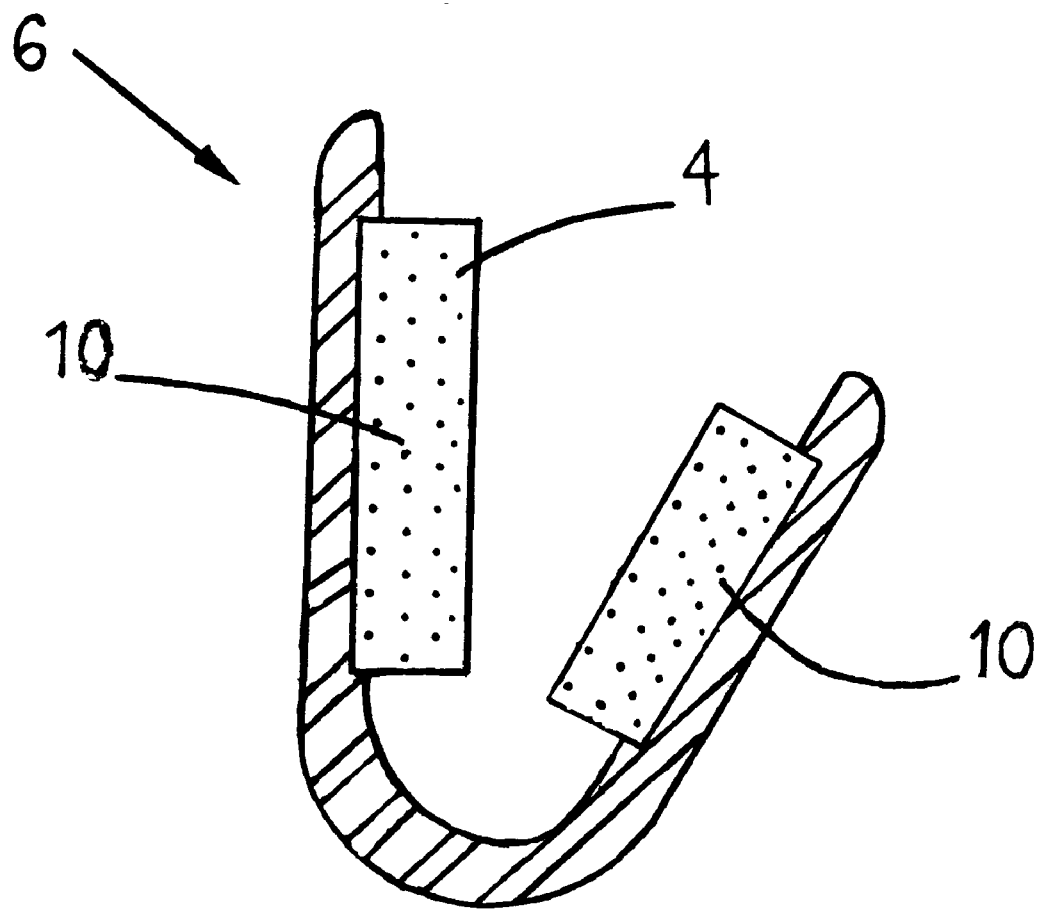
FIG. 2 illustrates a transverse cross-sectional view of the dental appliance of the present invention having a strip of hydrophilic open cell foam affixed along the inner front and rear walls of the dental appliance.

FIG. 2 illustrates an embodiment of the present invention featuring dental appliance 6 that is fabricated from a flexible polymeric material wherein a first strip of open cell foam 10 is attached along the frontal inner wall of the dental appliance and a second strip of open cell foam strip 10' is attached along the rear inner wall of the dental appliance.

As with the dental appliance shown in FIG. 1, open cell foam strips 10 and 10' are hydrophilic polymers into which medicinal agent 4 is incorporated. The open cell foam composing both dental appliance 2 and open cell foam strips 10 and 10' is preferably a hydrophilic material that is preferably, for example, a hydrogel polymer such as the Medicell™ foams (commercially available from Hydromer, Inc., which is located in Branchburg, N.J.). These hydrophilic foams may be composed of polyurethane or polyvinylpyrrolidone that is chemically imbibed with various agents which, among other things, impart high absorptivity. In the embodiment illustrated in FIG. 2, medicinal agent 4 is incorporated in open cell foam strips 10 and 10' that are attached to the inner wall or walls of the dental appliance according to the present invention. In alternative embodiments, medicinal agent 4 may be predispensed in the trough. The medicinal agent may include the compositions and materials as defined herein, in dry or powdered, or hydrated form, e.g., as a gel or liquid.

In the procedure utilized in practicing the present invention, an appropriate prefabricated, disposable dental appliance 2 or 6 which fits around a user's dental arches is selected. The dental appliance is positioned intraorally with the trough aligned in a parallel fashion to the edges of the teeth, and the teeth then immersed in the trough. Correctly placed, the dental appliance covers the teeth and surrounding dental tissue.

Figure 3:
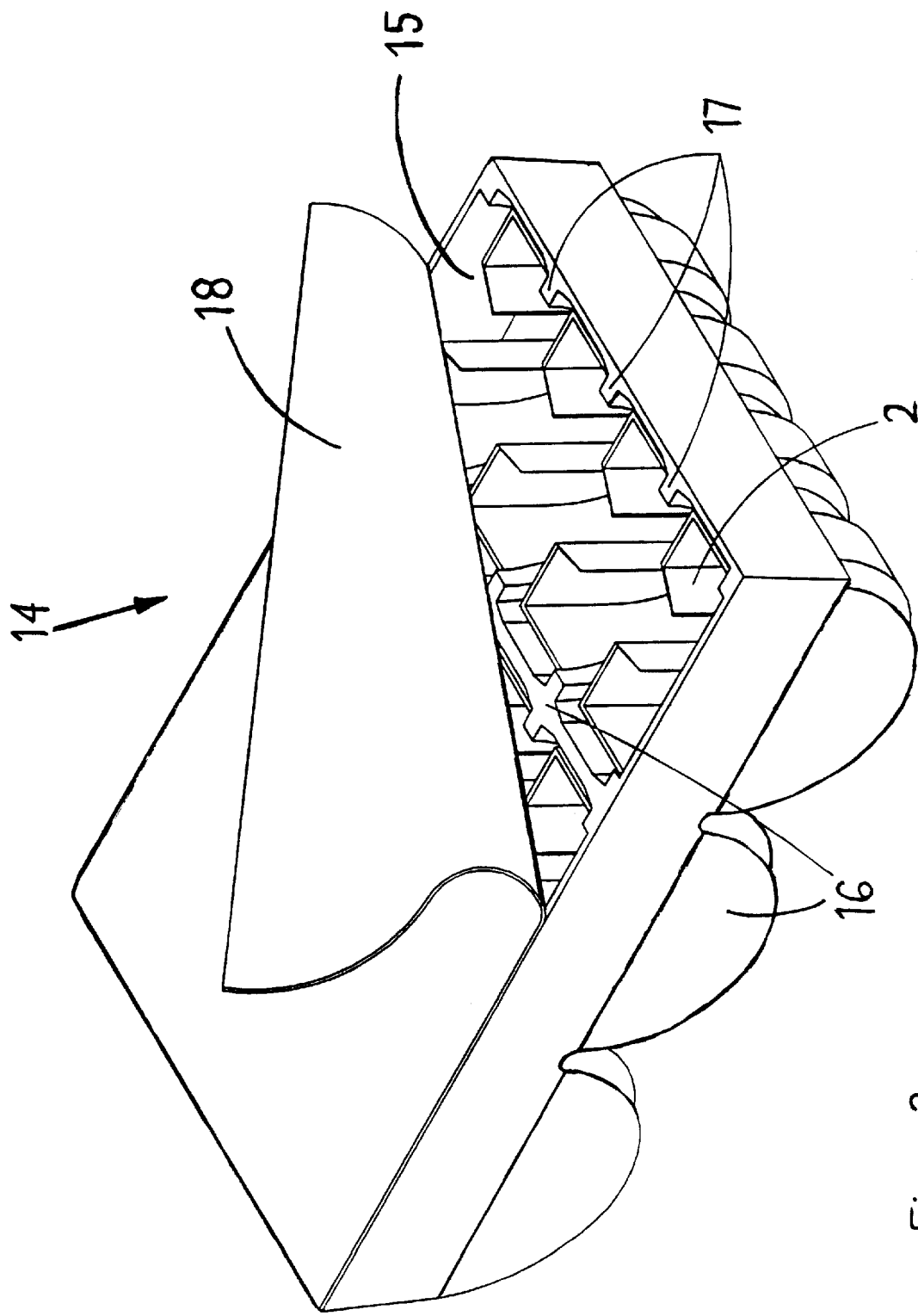
FIG. 3 shows a perspective view of packaging enclosing multiple dental appliances according to the present invention.

FIG. 3 depicts an alternative embodiment of the present invention wherein the packaging 14 is configured to contain multiple dental appliances. Packaging 14 is comprised of a lower rigid receptacle 16 with U-shaped cavities 15 configured to hold a dental appliance in its intended shape for fitting around a dental arch. The cavities 15 are joined by ledges 17 which are integrally connected to the cavity walls to form a planar horizontal surface to which an upper planar flexible sheet 18 is removable adhered. Sheet 18 is coated with adhesive at the points of contact with the ledges 17 of receptacle 16, thereby sealing the dental appliances placed therein within their respective cavities 15.

The dental appliance and packaging disclosed and shown herein are manufactured utilizing known automated and manual techniques for molding plastics, and suitable dispensing and manufacturing methods.

It is to be understood that the present invention is not intended to be limited to the exact details of construction, operation, exact materials or embodiments shown and described herein, as obvious modifications and equivalents will be apparent to one skilled in the art.

This disclosure is intended to cover all alternatives, modifications, and equivalents as may be included within the spirit and scope of the invention as defined by the appended claims. The following claims represent the scope of this invention to the extent that it is subject to such delimitations. It will be appreciated by those skilled in the art that the anticipated uses and embodiments of the present invention are not amenable to precise delineation, but may vary from the exact language of the claims. Thus, the following claims are drawn not only to the explicit limitations, but also to the implicit embodiments embraced by the spirit of the claims.

I claim:

1. A device for treatment of dental arches and periodontal tissue, comprising:
   (a) a dental appliance adaptable to fit a range of variously sized dental arches, the dental appliance having a trough for immersing the teeth of a dental arch, wherein the dental appliance comprises a hydrophilic open cell foam; and
   (b) a predetermined amount of medicinal agent incorporated in the hydrophilic foam prior to use.

2. The device of claim 1, wherein the hydrophilic open cell foam contains a predetermined amount of dry medicinal agent.

3. The device of claim 2, wherein the dry medicinal agent is carbamide peroxide.

4. The device of claim 1, wherein the dental appliance is encased by a nonporous flexible polymer.

5. The device of claim 1, wherein the hydrophilic open cell foam comprises a hydrogel polymer.

6. A device for treatment of the dental arches and periodontal tissue, comprising:
   (a) a dental appliance adaptable to fit a range of variously sized dental arches, the dental appliance having a trough for immersing the teeth of a dental arch; and
   (b) a polymeric packaging means for sealing the dental appliance to provide a closed system for application of a medicinal agent to the dental arches, wherein the packaging means resists permeation by water and bacterial contaminants.

7. The device of claim 6, wherein the packaging means comprises polyvinyl chloride.

8. The device of claim 6, wherein an open cell foam is attached to the frontal inner wall of the dental appliance and an open cell foam is attached to the rear inner wall of the dental appliance.

9. The device of claim 8, wherein the open cell foam is hydrophilic.

10. The device of claim 9, wherein the hydrophilic open cell foam incorporates a dry carbamide peroxide.

11. The device of claim 8, wherein the open cell foam incorporates a dry carbamide peroxide.

12. The device of claim 6, wherein an open cell foam is affixed along at least a portion of a frontal inner wall of the dental appliance for contacting the anterior portion of the dental arch subject to treatment.

13. The device of claim 12, wherein the open cell foam is hydrophilic.

14. The device of claim 13, wherein the trough of the dental appliance contains a predispensed amount of a medicinal agent.

15. The device of claim 13, wherein the hydrophilic open cell foam incorporates a dry carbamide peroxide.

16. The device of claim 12, wherein the open cell foam incorporates a dry carbamide peroxide.

17. The device of claim 6, wherein the dental appliance comprises an open cell foam.

18. The device of claim 17, wherein the open cell foam is hydrophilic.

19. The device of claim 18, wherein the trough of the dental appliance contains a predispensed amount of the medicinal agent.

20. The device of claim 18, wherein the hydrophilic open cell foam incorporates a dry carbamide peroxide.

21. The device of claim 17, wherein the open cell foam incorporates a dry carbamide peroxide.

22. The device of claim 6, wherein the trough of the dental appliance contains a predispensed amount of the medicinal agent.

* * * * *